United States Patent
Libbus et al.

(10) Patent No.: US 8,527,042 B2
(45) Date of Patent: *Sep. 3, 2013

(54) SYSTEM FOR ABATING NEURAL STIMULATION SIDE EFFECTS

(75) Inventors: Imad Libbus, St. Paul, MN (US); Julio C. Spinelli, Lakewood Ranch, FL (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/356,380

(22) Filed: Jan. 23, 2012

(65) Prior Publication Data

US 2012/0123494 A1 May 17, 2012

Related U.S. Application Data

(63) Continuation of application No. 11/467,264, filed on Aug. 25, 2006, now Pat. No. 8,103,341.

(51) Int. Cl.
*A61N 1/36* (2006.01)

(52) U.S. Cl.
USPC .................................. 607/2; 607/45; 607/118

(58) Field of Classification Search
None
See application file for complete search history.

(56) References Cited

U.S. PATENT DOCUMENTS

| | | | |
|---|---|---|---|
| 5,205,285 A | 4/1993 | Baker | |
| 5,330,515 A | 7/1994 | Rutecki et al. | |
| 6,141,587 A | 10/2000 | Mower | |
| 6,213,960 B1 | 4/2001 | Sherman et al. | |
| 6,480,743 B1 | 11/2002 | Kirkpatrick et al. | |
| 6,587,727 B2 | 7/2003 | Osorio et al. | |
| 6,615,085 B1 | 9/2003 | Boveja | |
| 6,671,556 B2 | 12/2003 | Osorio et al. | |
| 6,684,105 B2 | 1/2004 | Cohen et al. | |
| 6,920,357 B2 | 7/2005 | Osorio et al. | |
| 6,961,618 B2 | 11/2005 | Osorio et al. | |
| 7,050,856 B2 | 5/2006 | Stypulkowski | |
| 7,127,290 B2 | 10/2006 | Girouard et al. | |
| 7,623,926 B2 | 11/2009 | Rossing et al. | |

(Continued)

FOREIGN PATENT DOCUMENTS

| | | |
|---|---|---|
| JP | 2005-534406 A | 11/2005 |
| JP | 2006-116332 A | 5/2006 |

(Continued)

OTHER PUBLICATIONS

Australian Application Serial No. 2012200979, Office Action mailed Jun. 18, 2012, 3 pgs.

(Continued)

*Primary Examiner* — Carl H Layno
*Assistant Examiner* — Paula J Stice
(74) *Attorney, Agent, or Firm* — Schwegman Lundberg & Woessner, P.A.

(57) ABSTRACT

Various system embodiments comprise a neural stimulation delivery system adapted to deliver a neural stimulation signal for use in delivering a neural stimulation therapy, a side effect detector, and a controller. The controller is adapted to control the neural stimulation delivery system, receive a signal indicative of detected side effect, determine whether the detected side enact is attributable to delivered neural stimulation therapy, and automatically titrate the neural stimulation therapy to abate the side effect. In various embodiments, the side effect detector includes a cough detector. In various embodiments, the controller is adapted to independently adjusting at least one stimulation parameter for at least one phase in the biphasic waveform as part of a process to titrate the neural stimulation therapy. Other aspects and embodiments are provided herein.

20 Claims, 11 Drawing Sheets

(56) References Cited

U.S. PATENT DOCUMENTS

| | | | |
|---|---|---|---|
| 7,672,728 | B2 | 3/2010 | Libbus et al. |
| 8,103,341 | B2 | 1/2012 | Libbus et al. |
| 2003/0055461 | A1 | 3/2003 | Girouard et al. |
| 2004/0193231 | A1 | 9/2004 | David et al. |
| 2004/0199216 | A1 | 10/2004 | Lee et al. |
| 2004/0199217 | A1 | 10/2004 | Lee et al. |
| 2004/0199218 | A1 | 10/2004 | Lee et al. |
| 2004/0215288 | A1 | 10/2004 | Lee et al. |
| 2004/0215289 | A1 | 10/2004 | Fukui |
| 2004/0267330 | A1 | 12/2004 | Lee et al. |
| 2005/0060001 | A1 | 3/2005 | Singhal et al. |
| 2005/0060007 | A1 | 3/2005 | Goetz |
| 2005/0060008 | A1 | 3/2005 | Goetz |
| 2005/0060009 | A1 | 3/2005 | Goetz |
| 2005/0060010 | A1 | 3/2005 | Goetz |
| 2005/0070970 | A1 | 3/2005 | Knudson et al. |
| 2005/0075669 | A1 | 4/2005 | King |
| 2005/0085866 | A1 | 4/2005 | Tehrani |
| 2005/0115561 | A1 | 6/2005 | Stahmann et al. |
| 2005/0131486 | A1 | 6/2005 | Boveja et al. |
| 2005/0177206 | A1 | 8/2005 | North et al. |
| 2005/0197675 | A1 | 9/2005 | David et al. |
| 2005/0267542 | A1 | 12/2005 | David et al. |
| 2006/0015153 | A1 | 1/2006 | Gliner et al. |
| 2006/0052831 | A1 | 3/2006 | Fukui |
| 2006/0116737 | A1 | 6/2006 | Libbus |
| 2006/0129202 | A1 | 6/2006 | Armstrong |
| 2006/0190053 | A1 | 8/2006 | Dobak |
| 2008/0051839 | A1 | 2/2008 | Libbus et al. |

FOREIGN PATENT DOCUMENTS

| | | | |
|---|---|---|---|
| NO | WO-2005/011805 | A2 | 2/2005 |
| WO | WO-2004/012815 | A1 | 2/2004 |
| WO | WO-2006/044793 | A2 | 4/2006 |
| WO | WO-2008024557 | A1 | 2/2008 |

OTHER PUBLICATIONS

Chinese Application Serial No. 200780031534.9, Office Action mailed Feb. 16, 2012, (w/ English Translation), 26 pgs.

Chinese Application Seriai No. 200780031534.9, Office Action mailed Jul. 6, 2012, (w/ English Translation), 8 pgs.

Chinese Application Serial No. 200780031534.9, Response filed May 2, 2012 to Office Action mailed Feb. 16, 2012, (w/ English Translation of Claims), 11 pgs.

Japanese Application Serial No. 2009-525669, Office Action mailed Mar. 22, 2012, (w/ English Translation), 9 pgs.

Japanese Application Serial No. 2009-525669, Response filed Jul. 23, 2012 to Office Action mailed Mar. 22, 2012, (w/ English Translation of Amended Claims), 8 pgs.

"U.S. Appl. No. 11/467,264 Non-Final Office Action mailed Sep. 15, 2010", 7 pgs.

"U.S. Appl. No. 11/467,264, Examiner Interview Summary mailed Jul. 14, 2010", 3 pgs.

"U.S. Appl. No. 11/467,264, Final Office Action mailed May 10, 2010", 16 pgs.

"U.S. Appl. No. 11/467,264, Final Office Action mailed Aug. 3, 2011", 9 pgs.

"U.S. Appl. No. 11/467,264, Non Final Offi Action mailed Feb. 9, 2011", 8 pgs.

"U.S. Appl. No. 11/467,264, Non-Final Office Action mailed Dec. 18, 2009", 14 pgs.

"U.S. Appl. No. 11/467,264, Notice of Allowance mailed Sep. 28, 2011", 11 pgs.

"U.S. Appl. No. 11/467,264, Response filed Jun. 9, 2011 to Non Final Office Action mailed Feb. 9, 2011", 13 pgs.

"U.S. Appl. No. 11/467,264, Response filed Dec. 15, 2010 to Non Final Office Action mailed Sep. 15, 2010", 11 pgs.

"U.S. Appl. No. 11/467,264, Response filed Mar. 16, 2010 to Non Final Office Action mailed Dec. 18, 2010", 16 pgs.

"U.S. Appl. No. 11/467,264, Response filed Aug. 10, 2010 to Final Office Action mailed May 10, 2010", 16 pgs.

"U.S. Appl. No. 11/467,264, Response to Restriction Requirement, filed Dec. 8, 2009", 14 pgs.

"U.S. Appl. No. 11/467,264, Restriction Requirement mailed Nov. 9, 2009", 7 pgs.

"Australian Application Serial No. 2007287006, First Examiner Report mailed Aug. 13, 2010", 3 pgs.

"Australian Application Serial No. 2007287006, Response filed May 13, 2011 to First Examiner Report mailed Aug. 13, 2010", 22 pgs.

"Australian Application Serial No. 2007287006, Response filed Oct. 7, 2011 to Office Action mailed Jun. 20, 2011", 18 pgs.

"Australian Application Serial No. 2007287006, Subsequent Examiner Report mailed Jun. 20, 2011", 4 pgs.

"Chinese Application Serial No. 200780031534.9, Response filed Jul. 25, 2011 to Non Final Office Action dated Mar. 14, 2011", 16 pgs.

"Chinese Application Serial No. 200780031534.9, Office Action mailed Mar. 14, 2011", 7 pgs.

"PCT Application Serial No. PCT/US2007/072444, International Search Report mailed Dec. 5, 2007", 4 pgs.

"PCT Application Serial No. PCT/US2007/072444, Written Opinion mailed Dec. 5, 2007", 7 pgs.

Abraham, W. T., et al., "Cardiac Resynchronization in Chronic Heart Fahure", The New York Journal of Medicine, 346(24), (2002), 1845-1853.

Cyberonics, "NeuroCybernetic Prosthesis System NCPA Pulse Generator Models 100 and 101", Physician's Manual, (Aug. 2002), 1-146.

Nolan, J., et al., "Prospective Study of Heart Rate Variability and Mortality in Chronic Heart Failure: Results of the United Kingdom Heart Failure Evaluation and Assessment of Risk Trial (UK-Heart).", Circulation, 98(15), (1998), 1510-1516.

Sigurdsson, A., et al., "The Role of Neurohormonal Activation in Chronic Heart Failure and Postmyocardial Infarction", American Heart Journal, 132(1, Part 2), (Jul. 1996), 229-234.

Vanoli, E., et al., "Vagal Stimulation and Prevention of Sudden Death in Conscious Dogs With a Healed Myocardial Infarction", Circulation Research, 68(5), (May 1991), 1471-1481.

"Australian Application Serial No. 2012200979, Response filed Feb. 25, 2013 to First Examiner Report mailed Jun. 18, 2012", 27 pgs.

"Chinese Application Serial No. 200780031534.9, Response filed Sep. 19, 2012 to Office Action mailed Jul. 6, 2012", With English Claims, 7 pgs.

"Japanese Application Serial No. 2009-525669, Non Final Office Action dated Dec. 5, 2012", With English Translation, 5.

US 8,527,042 B2

SYSTEM FOR ABATING NEURAL STIMULATION SIDE EFFECTS

CLAIM OF PRIORITY

This application is a continuation of and claims the benefit of priority under 35 U.S.C. §120 to U.S. patent application Ser. No. 11/467,264, entitled "SYSTEM FOR ABATING NEURAL STIMULATION SIDE EFFECTS," filed on Aug. 25, 2006, now issued as U.S. Pat. No. 8,103,341, which is hereby incorporated by reference herein in its entirety.

FIELD

This application relates generally to medical devices and, more particularly, to systems, devices and methods for reducing potential side effects from neural stimulation.

BACKGROUND

Neural stimulation has been proposed as a therapy for a number of conditions. Examples of neural stimulation therapies include neural stimulation therapies for respiratory problems such a sleep disordered breathing, blood pressure control such as to treat hypertension, cardiac rhythm management, myocardial infarction and ischemia, heart failure, epilepsy, depression, pain, migraines, eating disorders and obesity, and movement disorders.

Many proposed neural stimulation therapies include stimulation of a diverse nerve, such as the vagus nerve. The vagus nerve innervates a number of organs. However, stimulation of the vagus nerve can have unintended consequences. For example, it has been reported that stimulation of the vagus nerve may cause an altered voice, coughing, pharyngitis, paresthesia, dyspnea, dyspepsia, nausea and laryngismus.

SUMMARY

Various aspects of the present subject matter relate to a system. Various system embodiments comprise a neural stimulation delivery system adapted to deliver a neural stimulation signal for use in delivering a neural stimulation therapy, a cough detector adapted to receive a signal from a cough sensor for use in detecting a cough, and a controller. The controller is adapted to control the neural stimulation delivery system, receive a signal indicative of detected cough from the cough detector, determine whether the detected cough is attributable to delivered neural stimulation therapy, and automatically titrate the neural stimulation therapy to abate the cough. Various system embodiments comprise a neural stimulation delivery system, a side effect detector, and a controller. The neural stimulation delivery system is adapted to deliver a neural stimulation signal for use delivering a neural stimulation therapy. The neural stimulation has a biphasic waveform with a first phase and a second phase. The side effect detector is adapted to receive a signal for use in detecting a side effect. The controller adapted to control the neural stimulation delivery system, receive a signal indicative of detected side effect from the side effect detector, determine whether the detected side effect is attributable to delivered neural stimulation therapy, and automatically titrate the neural stimulation therapy to abate the side effect including independently adjusting at least one stimulation parameter for at least one phase in the biphasic waveform.

Various aspects of the present subject matter relate to a method. According to various embodiments of the method, a neural stimulation therapy is applied. It is determined whether the neural stimulation therapy causes a cough, and the neural stimulation therapy is titrated to abate the cough caused by the neural stimulation therapy. According to various embodiments of the method, a neural stimulation therapy is applied using a biphasic neural stimulation waveform. It is determined whether the neural stimulation therapy causes a side effect. The neural stimulation therapy is titrated to abate the side effect caused by the neural stimulation therapy. At least one phase-specific stimulation parameter in the biphasic waveform is adjusted to provide the therapy titration.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1:
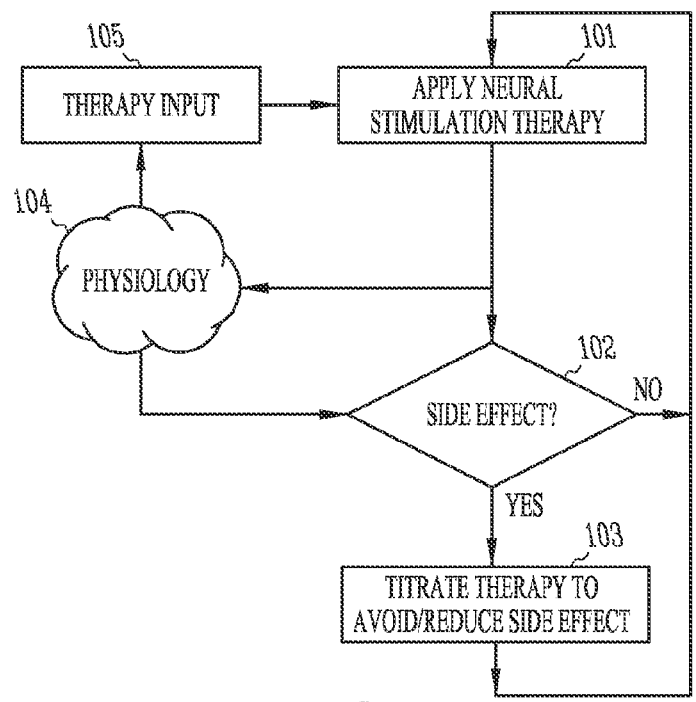
FIG. 1 illustrates an embodiment of a process to abate side effects when neural stimulation is applied.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Embodiments of the present subject matter provide a device that is capable of sensing and abating adverse side effects by automatically adjusting stimulation intensity. As used herein, the term "abating" as used in "abating side effects" includes terminating the sensed side effect, reducing the intensity of the sensed side effect, reducing the intensity of potential future side effects, and avoiding or preventing potential future side effects. For example, the neural stimulation intensity can be reduced below a side-effect threshold white maintaining stimulation at a therapeutic level. As will be evident to one for ordinary skill in the art, upon reading and comprehending this disclosure, the present subject matter can be implemented with various neural stimulation therapies. For example, some embodiments of the present subject matter provide an implantable vagal nerve stimulator to provide anti-remodeling therapy in heart failure or post myocardial infarction (post-MI) patients.

Various embodiments provide an implantable system to stimulate the vagus nerve using, for example, a cuff around the vagus nerve or an intravascular lead placed proximal to the nerve, such as within an internal jugular vein (IJV). Neural stimulation can be intermittently provided to the target nerve using a cyclical ON/OFF time. The device senses for adverse side effects when neural stimulation is applied. Various embodiments sense for the presence of coughing, a common adverse side effect. Coughing can be characterized as a sudden, violent chest movement, and may be detected with a variety of different sensors, such as an accelerometer or acoustic sensor. Upon detection of the side effect, the intensity of neural stimulation is automatically adjusted below the side-effect threshold. The stimulation intensity can be adjusted by adjusting the amplitude, frequency, duty cycle, and/or pulse width of the neural stimulation signal (including for a phase of a biphasic waveform). The side-effect threshold may increase over time, and the intensity of the neural stimulation therapy can increase with it while remaining below the side-effect threshold.

In a biphasic wave form, the amplitude and pulse width of the second phase has been shown to modulate side effects at a fixed first phase. Amplitude and pulse width of both phases may be independently titrated to avoid side effects while maintaining stimulation at a therapeutic level. Various embodiments deliver neural stimulation with a train of charge-balanced biphasic pulses, and adjust the amplitude and pulse width of the second phase to avoid side effects while maintaining the amplitude and pulse width of the first phase at a therapeutic level. The device can deliver a charge-balanced waveform, or balanced within a specified percentage or threshold, to avoid charge build-up that may damage nerves over time. The device may also contain an independent maximum limit on neural stimulation intensity.

Physiology

The nervous system can be used to provide therapy for heart failure, hypertension, cardiac remodeling, and physical conditioning therapy. These are briefly discussed below.

Nervous System

The automatic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Afferent nerves convey impulses toward a nerve center, and efferent nerves convey impulses away from a nerve center.

The heart rate and force is increased when the sympathetic nervous system is stimulated, and is decreased when the sympathetic nervous system is inhibited (the parasympathetic nervous system is stimulated). Cardiac rate, contractility, and excitability are known to be modulated by centrally mediated reflex pathways. Baroreceptors and chemoreceptors in the heart, great vessels, and lungs, transmit cardiac activity through vagal and sympathetic afferent fibers to the central nervous system. Activation of sympathetic afferents triggers reflex sympathetic activation, parasympathetic inhibition, vasoconstriction, and tachycardia. In contrast, parasympathetic activation results in bradycardia, vasodilation, and inhibition of vasopressin release. Among many other factors, decreased parasympathetic or vagal tone or increased sympathetic tone is associated with the genesis of various arrhythmias, including ventricular tachycardia and atrial fibrillation.

Baroreflex is a reflex triggered by stimulation of a baroreceptor. A baroreceptor includes any sensor of pressure changes, such as sensory nerve endings in the wall of the auricles of the heart, vena cava, aortic arch and carotid sinus, that is sensitive to stretching of the wall resulting from increased pressure from within, and that functions as the receptor of the central reflex mechanism that tends to reduce that pressure. Clusters of nerve cells can be referred to as autonomic ganglia. These nerve cells can also be electrically stimulated to induce a baroreflex, which inhibits the sympathetic nerve activity and stimulates parasympathetic nerve activity. Autonomic ganglia thus forms part of a baroreflex pathway. Afferent nerve trunks, such as the vagus, aortic and carotid nerves, leading from the sensory nerve endings also form part of a baroreflex pathway. Stimulating a baroreflex pathway and/or baroreceptors inhibits sympathetic nerve activity (stimulates the parasympathetic nervous system) and reduces systemic arterial pressure by decreasing peripheral vascular resistance and cardiac contractility. Baroreceptors are naturally stimulated by internal pressure and the stretching of vessel wall (e.g. arterial wall).

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other.

Neural stimulation can be used to stimulate nerve traffic or inhibit nerve traffic. An example of neural stimulation to stimulate nerve traffic is a lower frequency signal (e.g. within a range on the order of 20 to 50 Hz). An example of neural stimulation to inhibit nerve traffic is a higher frequency signal (e.g. within a range on the order of 120 to 150 Hz). Other methods for stimulating and inhibiting nerve traffic have been proposed, including anodal block of nerve traffic. According to various embodiments of the present subject matter, sympathetic neural targets include, but are not limited to, a peroneal nerve, a sympathetic column in a spinal cord, and cardiac post-ganglionic sympathetic neurons. According to various embodiments of the present subject matter, parasympathetic neural targets include, but are not limited to, a vagus nerve, a baroreceptor, and a cardiac fat pad.

Heart Failure

Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease.

Heart failure patients have reduced autonomic balance, which is associated with LV dysfunction and increased mortality. Modulation of the sympathetic and parasympathetic nervous systems has potential clinical benefit in preventing remodeling and death in heart failure and post-MI patients. Direct electrical stimulation can activate the baroreflex, inducing a reduction of sympathetic nerve activity and reducing blood pressure by decreasing vascular resistance. Sympathetic inhibition and parasympathetic activation have been associated with reduced arrhythmia vulnerability following a myocardial infarction, presumably by increasing collateral perfusion of the acutely ischemic myocardium and decreasing myocardial damage.

Hypertension

Hypertension is a cause of heart disease and other related cardiac co-morbidities. Hypertension occurs when blood vessels constrict. As a result, the heart works harder to maintain flow at a higher blood pressure, which can contribute to heart failure. Hypertension generally relates to high blood pressure, such as a transitory or sustained elevation of systemic arterial blood pressure to a level that is likely to induce cardiovascular damage or other adverse consequences. Hypertension has been arbitrarily defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease.

A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

Cardiac Remodeling

Following myocardial infarction (MI) or other cause of decreased cardiac output, a complex remodeling process of the ventricles occurs that involves structural, biochemical, neurohormonal, and electrophysiologic factors. Ventricular remodeling is triggered by a physiological compensatory mechanism that acts to increase cardiac output due to so-called backward failure which increases the diastolic filling pressure of the ventricles and thereby increases the preload the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation.

As the heart begins to dilate, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

Therapies

The present subject matter relates to systems, devices and methods for providing neural stimulation, such as vagus nerve stimulation, and further relates to terminating, preventing, or diminishing potential side effects of neural stimulation. Various embodiments provide a stand-alone device, either externally or internally, to provide neural stimulation therapy. The present subject matter can be implemented in cardiac applications for neural stimulation or in non-cardiac applications for neural stimulation where a diverse nerve (such as the vagus nerve) is stimulated. For example, the present subject matter may deliver anti-remodeling therapy through neural stimulation as part of a post-MI or heart failure therapy. The present subject matter may also be implemented in non-cardiac applications, such as in therapies to treat epilepsy, depression, pain, obesity, hypertension, sleep disorders, and neuropsychiatric disorders. Various embodiments provide systems or devices that integrate neural stimulation with one or more other therapies, such as bradycardia pacing, anti-tachycardia therapy, remodeling therapy, and the like.

Neural Stimulation Therapies

Examples of neural stimulation therapies include neural stimulation therapies for respiratory problems such a sleep disordered breathing, for blood pressure control such as to treat hypertension, for cardiac rhythm management, for myocardial infarction and ischemia, for heart failure, for epilepsy, for depression, for pain, for migraines, for eating disorders and obesity, and for movement disorders. Many proposed neural stimulation therapies include stimulation of the vagus nerve. This listing of other neural stimulation therapies is not intended to be an exhaustive listing. Neural stimulation can be provided using electrical, acoustic, ultrasound, light, and magnetic therapies. Electrical neural stimulation can be delivered using any of a nerve cuff, intravascularly-fed lead, or transcutaneous electrodes.

Neural Stimulation for Ventricular Remodeling

A therapy involves preventing and/or treating ventricular remodeling. Activity of the autonomic nervous system is at least partly responsible for the ventricular remodeling which occurs as a consequence of an MI or due to heart failure. It has been demonstrated that remodeling can be affected by pharmacological intervention with the use of, for example, ACE inhibitors and beta-blockers. Pharmacological treatment carries with it the risk of side effects, however, and it is also difficult to modulate the effects of drugs in a precise manner. Embodiments of the present subject matter employ electro-stimulatory means to modulate autonomic activity, referred to as anti-remodeling therapy or ART. When delivered in conjunction with ventricular resynchronization pacing, also referred to as remodeling control therapy (RCT), such modulation of autonomic activity acts synergistically to reverse or prevent cardiac remodeling.

Hypertension

One neural stimulation therapy involves treating hypertension by stimulating the baroreflex for sustained periods of time sufficient to reduce hypertension. The baroreflex is a reflex that can be triggered by stimulation of a baroreceptor or an afferent nerve trunk. Baroreflex neural targets include any sensor of pressure changes, such as sensory nerve endings in the wall of the auricles of the heart, cardiac fat pads, vena cava, aortic arch and carotid sinus, that is sensitive to stretching of the wall resulting from increased pressure from within, and that functions as the receptor of the central reflex mechanism that tends to reduce that pressure. Examples of afferent nerve trunks that can serve as baroreflex neural targets include the vagus, aortic and carotid nerves. Stimulating baroreceptors inhibits sympathetic nerve activity (stimulates the parasympathetic nervous system) and reduces systemic arterial pressure by decreasing peripheral vascular resistance and cardiac contractility. Baroreceptors are naturally stimulated by internal pressure and the stretching of the arterial wall. Some aspects of the present subject matter locally stimulate specific nerve endings in arterial walls rather than stimulate afferent nerve trunks in an effort to stimulate a desire response (e.g. reduced hypertension) while reducing the undesired effects of indiscriminate stimulation of the nervous system. For example, some embodiments stimulate baroreceptor sites in the pulmonary artery. Some embodiments of the present subject matter involve stimulating either baroreceptor sites or nerve endings in the aorta, the chambers of the heart, the fat pads of the heart, and some embodiments of the present subject matter involve stimulating an afferent nerve trunk, such as the vagus, carotid and aortic nerves. Some embodiments stimulate afferent nerve trunks using a cuff electrode, and some embodiments stimulate afferent nerve trunks using an intravascular lead positioned in a blood vessel proximate to the nerve, such that the electrical stimulation passes through the vessel wall to stimulate the afferent nerve trunk, Physical Conditioning Therapy Neural stimulation (e.g. sympathetic nerve stimulation and/or parasympathetic nerve inhibition) can mimic the effects of physical conditioning. It is generally accepted that physical activity and fitness improve health and reduce mortality. Studies have indicated that aerobic training improves cardiac autonomic regulation, reduces heart rate and is associated with increased cardiac vagal outflow. A baseline measurement of higher parasympathetic activity is associated with improved aerobic fitness. Exercise training intermittently stresses the system and increases the sympathetic activity during the stress. However, when an exercise session ends and the stress is removed, the body rebounds in a manner that increases baseline parasympathetic activity and reduces baseline sympathetic activity. Physical conditioning can be considered to be a repetitive, high-level exercise that occurs intermittently over time.

Physical conditioning therapy can be applied as therapy for heart failure. Examples of other physical conditioning therapies include therapies for patients who are unable to exercise. For example, physical conditioning using sympathetic stimulation/parasympathetic inhibition for a bed-bound, post-surgical patient in a hospital may enable the patient to maintain strength and endurance until such time that the patient is able to exercise again. By way of another example, a morbidly obese patient may be unable to exercise, but may still benefit from the physical conditioning therapy. Furthermore, patients with injuries such as joint injuries that prevent them from performing their normal physical activities may benefit from the physical conditioning therapy.

Myocardial Stimulation Therapies

Various neural stimulation therapies can be integrated with various myocardial stimulation therapies. The integration of therapies may have a synergistic effect. Therapies can be synchronized with each other, and sensed data can be shared between the therapies. A myocardial stimulation therapy provides a cardiac therapy using electrical stimulation of the myocardium. Some examples of myocardial stimulation therapies are provided below.

A pacemaker is a device which paces the heart with timed pacing pulses, most commonly for the treatment of bradycardia where the ventricular rate is too slow. If functioning properly, the pacemaker makes up for the heart's inability to pace itself at an appropriate rhythm in order to meet metabolic demand by enforcing a minimum heart rate. Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace.

CRT can be beneficial in reducing the deleterious ventricular remodeling which can occur in post-MI and heart failure patients. Presumably, this occurs as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions is most probably the trigger for ventricular remodeling. By pacing one or more sites in a ventricle near the infarcted region in a manner which may cause a more coordinated contraction, CRT provides pre-excitation of myocardial regions which would otherwise be activated later during systole and experience increased wall stress. The pre-excitation of the remodeled region relative to other regions unloads the region from mechanical stress and allows reversal or prevention of remodeling to occur.

Cardioversion, an electrical shock delivered to the heart synchronously with the QRS complex, and defibrillation, an electrical shock delivered without synchronization to the QRS complex, can be used to terminate most tachyarrhythmias. The electric shock terminates the tachyarrhythmia by simultaneously depolarizing the myocardium and rendering it refractory. A class of CRM devices known as an implantable cardioverter defibrillator (ICD) provides this kind of therapy by delivering a shock pulse to the heart when the device detects tachyarrhythmias. Another type of electrical therapy for tachycardia is anti-tachycardia pacing (ATP). In ventricular ATP, the ventricles are competitively paced with one or more pacing pulses in an effort to interrupt the reentrant circuit causing the tachycardia. Modern ICDs typically have ATP capability, and deliver ATP therapy or a shock pulse when a tachyarrhythmia is detected.

Method Embodiments for Reducing or Preventing Neural Stimulation Side Effects

FIG. 1 illustrates an embodiment of a process to abate side effects when neural stimulation is applied. A neural stimulation therapy is applied at 101. According to various embodiments, the neural stimulation is turned on and off during a therapy schedule, and includes a train of pulses when the stimulation is turned on. At 102, it is determined whether a side effect attributable to the neural stimulation is detected. In various embodiments, for example, it is determined whether the neural stimulation and side effects occur at or near the same time to determine that the neural stimulation causes the side effect. If a side effect is not detected, the process returns to 101 to continue to apply the neural stimulation therapy. If a side-effect is detected, the process proceeds to 103 where the intensity of the neural stimulation therapy is titrated to abate (avoid or diminish) the side effect. Some examples for titrating the neural stimulation therapy intensity are provided below with respect to FIG. 8.

Neural stimulation affects physiology 104 through a neural network. Therapy inputs 105 can be sensed or derived using physiology sensors, which can provide a feedback signal used to control the applied neural stimulation therapy. Physiology sensors or other inputs can be used to sense, determine or otherwise derive that a side effect is occurring, as illustrated at 102. For example, an embodiment includes a cough sensor adapted to determine when a cough is attributable to applied neural stimulation. Other embodiments use patient or doctor input for use in determining when a patient is experiencing a side effect attributable to the neural stimulation.

Figure 2:
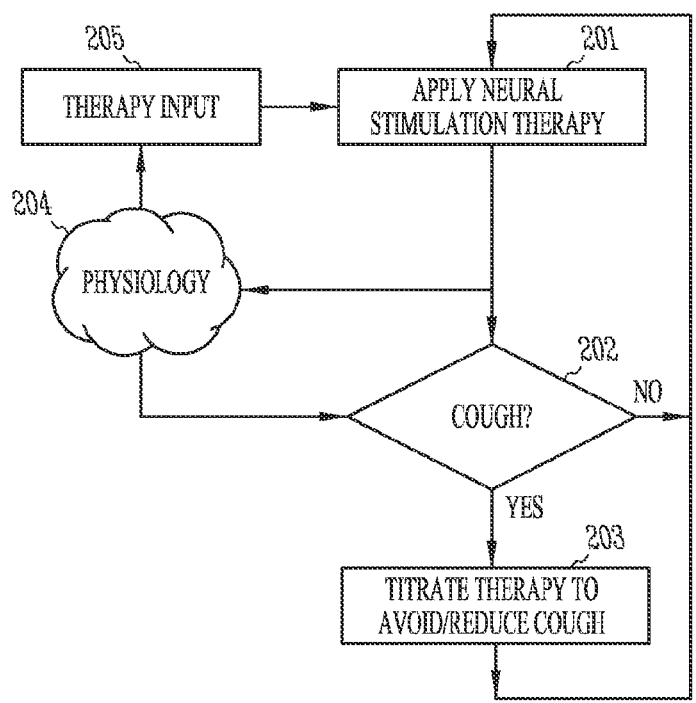
FIG. 2 illustrates an embodiment of a process to abate a cough when neural stimulation therapy is applied.

FIG. 2 illustrates an embodiment of a process to abate a cough when neural stimulation therapy is applied. A neural stimulation therapy is applied at 201. According to various embodiments, the neural stimulation is turned on and off during a therapy schedule, and includes a train of pulses when the stimulation is turned on. At 202, it is determined whether a cough attributable to the neural stimulation is detected. In various embodiments, it is determined whether the neural stimulation and cough occurs simultaneously to determine that the neural stimulation causes the cough. If a cough is not detected, the process returns to 201 to continue to apply the neural stimulation therapy. If a cough attributable to the neural stimulation is detected, the process proceeds to 203 where the intensity of the neural stimulation therapy is titrated to abate (avoid or diminish) the side effect. Examples for titrating the neural stimulation therapy intensity are provided below with respect to FIG. 8.

Neural stimulation affects physiology 204 through a neural network. Therapy inputs 205 can be sensed or derived using physiology sensors, which can provide a feedback signal used to control the applied neural stimulation therapy. Physiology sensors or other inputs can be used to sense, determine or otherwise derive that a cough is occurring, as illustrated at 202. An example of a cough sensor includes an accelerometer capable of detecting a chest movement that can be characterized as a sudden and violent movement indicative of a cough. For example, once a movement exceeds a threshold, it can be determined that a cough occurred. Another example of a cough sensor includes an acoustic detector capable of detecting a cough sound. For example, once a sound exceeds a threshold, it can be determined that a cough occurred. Other criteria can be placed on the movement or sound to identify coughs. Various embodiments combine an accelerometer and an acoustic sensor to sense a cough.

Figure 3:
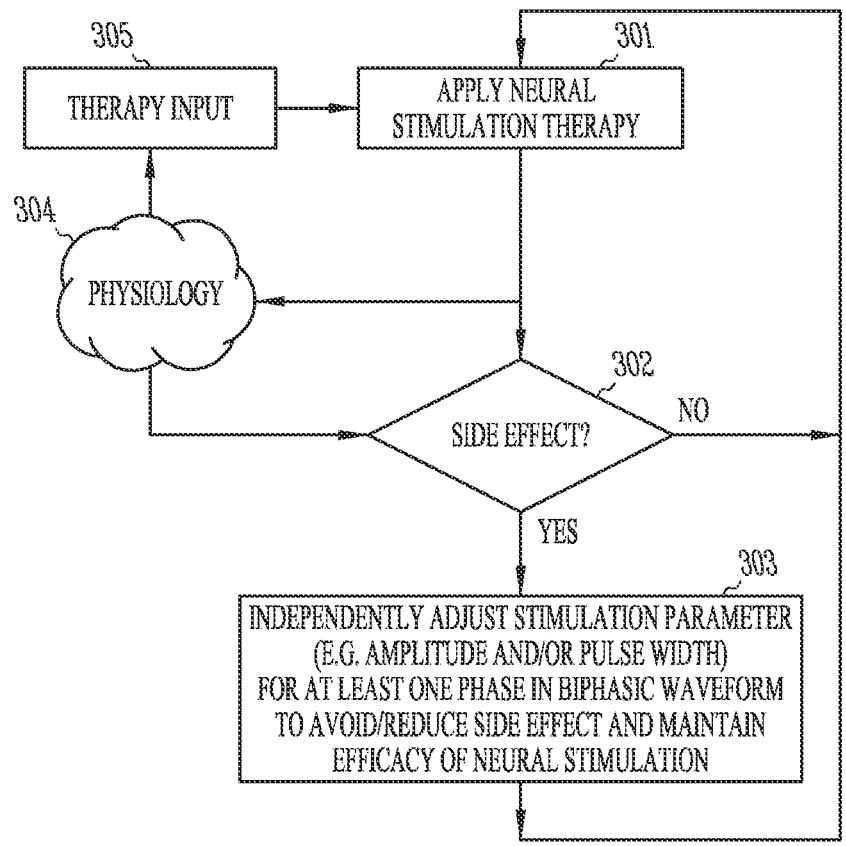
FIG. 3 illustrates an embodiment of a process to abate side effects when neural stimulation is applied that includes independently adjusting at least one stimulation parameter for at least one phase in a biphasic waveform.

FIG. 3 illustrates an embodiment of a process to abate side effects when neural stimulation is applied that includes independently adjusting at least one stimulation parameter for at least one phase in a biphasic waveform. A neural stimulation therapy is applied at 301. According to various embodiments, the neural stimulation is turned on and off during a therapy schedule, and includes a train of pulses when the stimulation is turned on. At 302, it is determined whether a side effect attributable to the neural stimulation is detected. In various embodiments, it is determined whether the neural stimulation and side effects occurs simultaneously to determine that the neural stimulation causes the side effect. If a side effect is not detected, the process returns to 301 to continue to apply the neural stimulation therapy. If a side-effect is detected, the process proceeds to 303 where the intensity of the neural stimulation therapy is titrated to abate (avoid or diminish) the side effect. Neural stimulation affects physiology 304 through a neural network. Therapy inputs 305 can be sensed or derived using physiology sensors, which can provide a feedback signal used to control the applied neural stimulation therapy. Physiology sensors or other inputs can be used to sense, determine or otherwise derive that a side effect is occurring. Other embodiments use patient or doctor input for use in determining when a patient is experiencing a side effect attributable to the neural stimulation.

In the illustrated embodiment, the applied neural stimulation therapy 301 includes a biphasic waveform. The neural stimulation therapy is titrated 303 in the illustrated embodiment by independently adjusting stimulation parameters for at least one phase in the biphasic waveform. An embodiment adjusts an amplitude of at least one of the phases of the biphasic waveform as part of a process to titrate the neural stimulation therapy. An embodiment adjusts a pulse width of at least one of the phases of the biphasic waveform as part of the process to titrate the neural stimulation therapy. Various embodiments adjust both the amplitude and pulse width as part of the titration process.

Various embodiments adjust at least one of the phases to balance, within a specified percentage or threshold, the charges at the electrode/tissue interface. Charge (Q) and current (I) are related as follows: I=Q/second. Thus, larger current and/or longer pulse width times can cause higher charge build up at an electrode or electrodes, and smaller current and for smaller pulse width times can cause smaller charge build up at an electrode or electrodes.

Figure 4:
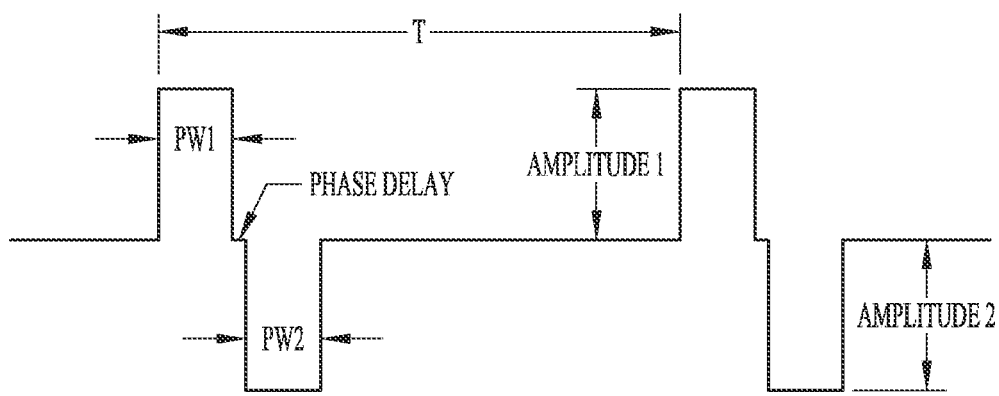
FIG. 4 illustrates a biphasic waveform with some parameters that can be adjusted in the process illustrated in FIG. 3.

FIG. 4 illustrates a biphasic waveform with some parameters that can be adjusted in the process illustrated in FIG. 3. Two biphasic pulses are illustrated. Each biphasic pulse includes a first phase (PW1 illustrated as a positive pulse) and a second phase (PW2 illustrated as a negative pulse). In the illustrated waveform, the first and second phases are separated by a phase delay. Various embodiments use a biphasic waveform with no phase delay (a phase delay that is zero). Each of the first and second phases of the pulse has an amplitude. According to embodiments of the present subject matter, stimulation parameters associated with the first and second phases can be independently adjusted. Thus, for example, the second phase can be adjusted while the first phase maintains the stimulation parameters. For example, the amplitude or magnitude of the second phase (PW2) can be reduced to avoid or reduce a side effect, and the pulse width can be lengthened to maintain a charge balance between the two phases.

FIG. 4 can illustrate either a current biphasic pulse waveform or a voltage biphasic pulse waveform. For a current biphasic pulse waveform, the charge is proportional to current (I) times the pulse width (PW), or Q=I*PW. Form given resistive load (R), current (I) and voltage (V) are related as V=IR. Thus, for a voltage biphasic pulse waveform, the charge is also proportional to voltage (V) time pulse width (PW), or Q=(V/R)*PW. Appropriate circuitry can be designed to predict or measure charge build up associated with each phase of the biphasic pulse, and to appropriately adjust at least one stimulation parameter for at least one of the phases of the biphasic pulse to maintain a balance (or a near balance within a threshold) of each other. For example, the area in each pulse can be calculated (area=amplitude*pulse width), and the stimulation parameter(s) for at least one phase are appropriately adjusted to generally equalize the areas in both phases, where one phase maintains therapeutic effectiveness of the neural stimulation and the other phase reduces or eliminates side effects.

Device Embodiments

Figure 5:
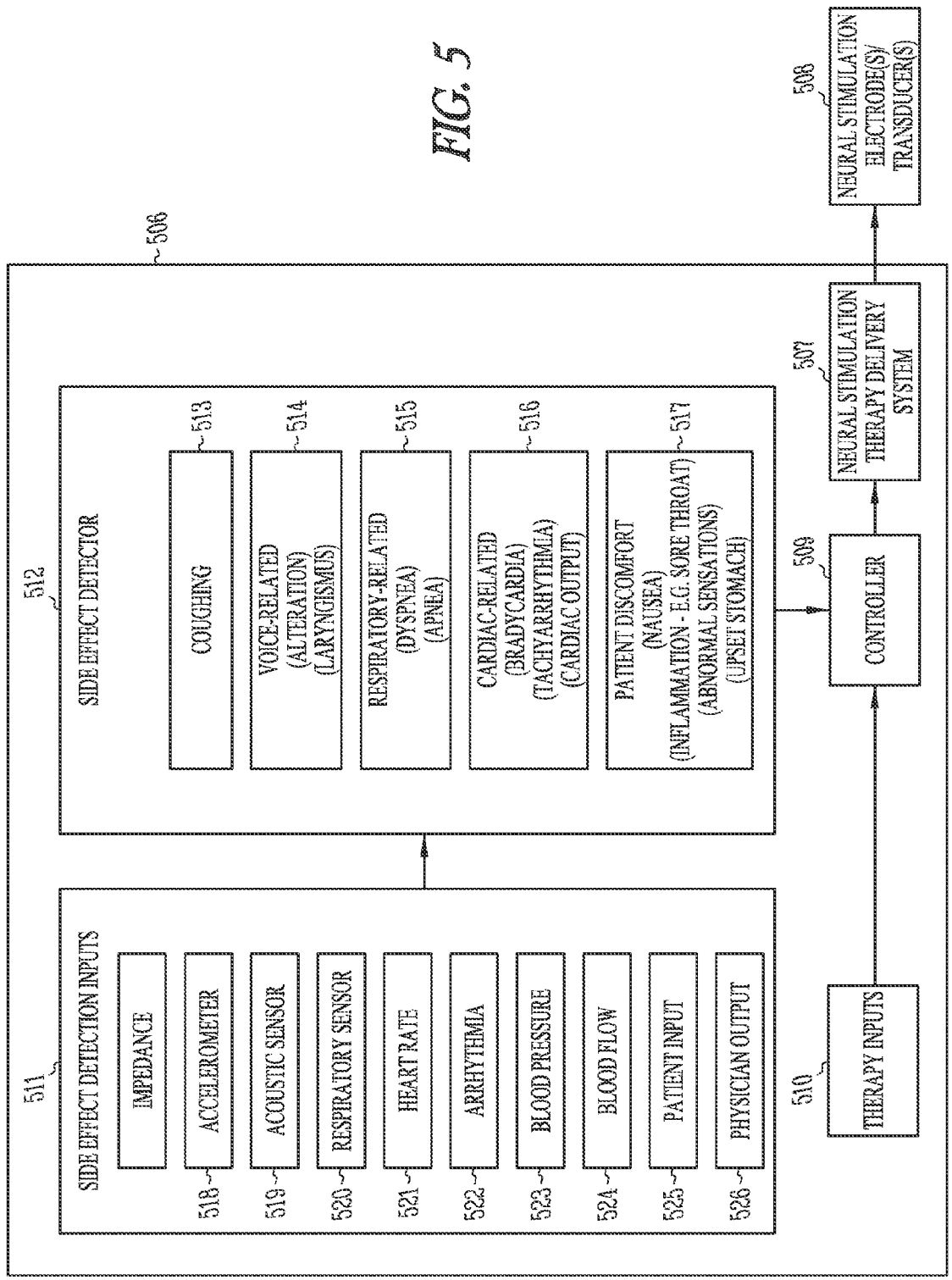
FIG. 5 illustrates a neural stimulator device embodiment adapted to abate neural stimulation side effects, according to various embodiments.

FIG. 5 illustrates a neural stimulator device embodiment adapted to abate neural stimulation side effects, according to various embodiments. The illustrated device 506 can be an implantable device or an external device. The illustrated device includes a neural stimulation delivery system 507 adapted to deliver a neural stimulation signal to the neural stimulation electrode(s) or transducer(s) 508 to deliver the neural stimulation therapy. Examples of neural stimulation electrodes include nerve cuff electrodes, intravascularly placed electrodes, and transcutaneous electrodes. Examples of neural stimulation transducers includes ultrasound, light and magnetic energy transducers. A controller 509 receives therapy inputs 510, and appropriately controls the neural stimulation therapy delivery system 507 using the therapy inputs 510 to provide the appropriate neural stimulation signal to the electrode(s)/transducer(s) that results in a desired intensity of neural stimulation.

The illustrated device also includes side-effect detection inputs 511 and a side event detector 512. Examples of side effects capable of being detected by the side effect detector 512 include coughing 513, voice-related side effects 514 such as voice alterations or laryngismus, respiratory-related side effects 515 such as dyspnea and apnea, cardiac-related side effects 516 such as bradycardia, tachyarrhythmias, and reduced cardiac output, and patient discomfort 517 such as nausea, inflammation of throat, abnormal sensations, and upset stomach. Various inputs 511 can be used by the side effect detector 512. For example, an impedance sensor, an accelerometer 518 and/or acoustic sensor 519 can be used to detect coughing. An acoustic sensor 519 can also be used to detect voice-related side effects. Respiratory sensors 520, such as minute ventilation and transthoracic impedance, can be used to detect respiratory-related side effects. Cardiac-related side effects can be detected using heart rate sensors 521, arrhythmia detectors 522, blood pressure sensors 523, and blood flow sensors 524. Patient discomfort can be determined by inputs from a patient 525 or physician 526. Advanced patient management systems can be used to enable the patient and/or doctor to provide the inputs. The inputs can be provided by computers, programmers, cell phones, personal digital assistants, and the like. For example, a patient can determine when an intolerable side effect is occurring, and report the side effect. The patient can call a call center using a regular telephone, a mobile phone, or the internet. The communication can be through a repeater, similar to that used in Guidant's Latitude patient management system. In response, the call center (e.g. server in call center) can automatically send information to the device to adjust or titrate the therapy. The call center can inform the patient's physician of the event. In various embodiments, a patient's report of side effect(s) triggers an interrogation of the device. The interrogation can be automatically triggered. The results of the device interrogation can be used to determine if and how the therapy should be adjusted and/or titrated to abate the side effect(s) reported by the patient. A server can automatically adjust and/or titrate the therapy using the results of the device interrogation. Medical staff can review the results of the device interrogation, and program the device through the remote server to provide the desired therapy adjustments and/or titrations. The server can communicate results of the device interrogation to the patient's physician, who can provide input or direction for adjusting and/or titrating the therapy. Combinations of these or other inputs can be used to determine whether a patient is experiencing a side effect. The controller 509 receives a side-effect control signal from the side effect detector. The controller uses the side-effect control signal to appropriately control the neural stimulation therapy delivery system to avoid or reduce side effects attributed to the neural stimulation. The controller is able to determine whether the timing of the experienced side effect corresponds to the timing of the neural stimulator, such that it can be deduced that the neural stimulation causes the observed side effect.

Figure 6:
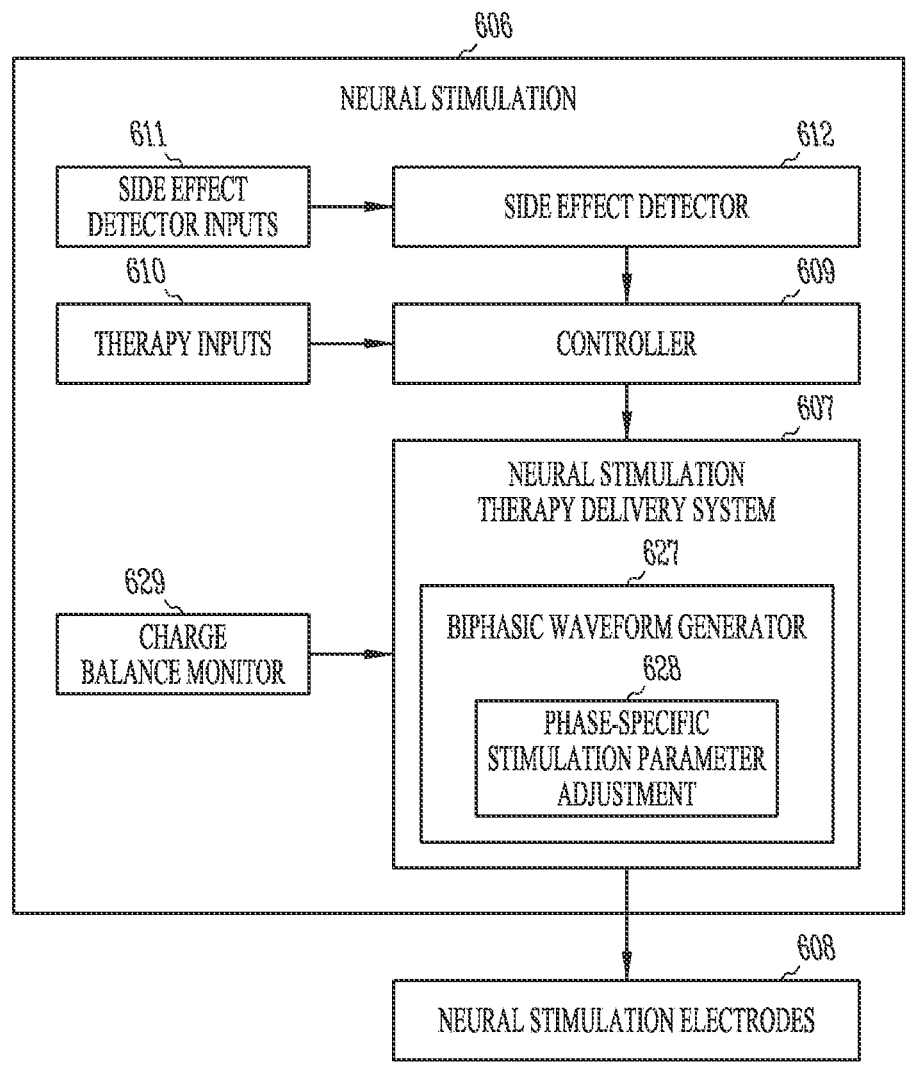
FIG. 6 illustrates a neural stimulator device embodiment adapted to adjust a phase specific stimulation parameter of a biphasic neural stimulation waveform to abate neural stimulation side effects, according to various embodiments.

FIG. 6 illustrates a neural stimulator device embodiment adapted to adjust a phase specific stimulation parameter of a biphasic neural stimulation waveform to abate neural stimulation side effects, according to various embodiments. The illustrated device 606 can be an implantable device or an external device. The illustrated device includes a neural stimulation delivery system 607 adapted to deliver a neural stimulation signal to the neural stimulation electrode(s) 608. Examples of neural stimulation electrodes include nerve cuff electrodes, intravascularly placed electrodes, and transcutaneous electrodes. A controller 609 receives therapy inputs 610, and appropriately controls the neural stimulation therapy delivery system 607 using the therapy inputs 610 to provide the appropriate neural stimulation signal to the electrode(s)/transducer(s) that results in a desired intensity of neural stimulation. The illustrated device also includes side-effect detection inputs 611 and a side event detector 612. Various inputs 611 can be used by the side effect detector 612 to determine when a side effect is being experienced. The controller 609 receives a side-effect control signal from the side effect detector 612. The controller uses the side-effect control signal to appropriately control the neural stimulation therapy delivery system to avoid or reduce side effects attributed to the neural stimulation. The controller is able to determine whether the timing of the experienced side effect corresponds to the timing of the neural stimulator, such that it can be deduced that the neural stimulation causes the observed side effect.

The neural stimulation therapy delivery system included in the illustrated device 606 includes a biphasic waveform generator 627, and a phase-specific stimulation parameter adjustment 628. Thus, for example, the generator includes means for independently adjusting stimulation parameter(s) for at least one phase in the biphasic waveform. Examples of adjustable stimulation parameters include an amplitude and/or pulse width of either phase of the biphasic pulse. The illustrated embodiment also includes a charge balance monitor 629, which provides an input to the phase-specific adjustment of the stimulation parameters for the biphasic waveform generator.

Figure 7:
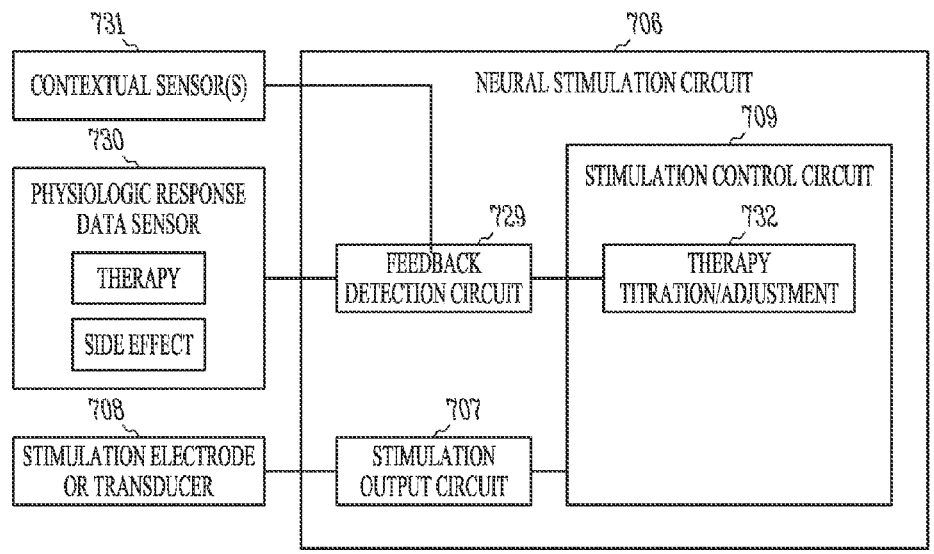
FIG. 7 illustrates an embodiment of a neural stimulator device.

FIG. 7 illustrates an embodiment of a neural stimulator device. The illustrated device 706 includes a stimulation output circuit 707 adapted to deliver a neural stimulation signal to the stimulation electrode(s) or transducer(s). A stimulation control circuit 709 receives a feedback signal from a feedback detection circuit 729, and appropriately controls the stimulation output circuit 707 to send a desired neural stimulation signal to the electrode or transducer 708 for use in delivering the neural stimulation therapy. The feedback detection circuit receives a signal from a physiologic response data sensor 730, which can include the appropriate therapy sensors to provide a closed loop for obtaining a desired therapy response and can include the appropriate sensors to detect a side effect. In various embodiments, the response from the physiologic response data sensor 730 includes a cardiac activity such as heart rate, HRV, HRT, or PR interval. In various embodiments the response includes a non-cardiac response such as respiration, blood pressure or cough. Contextual sensor(s) or input(s) 731 are also illustrated connected to the feedback detection circuit 729 to provide a more complete picture of a patient's physiology. The feedback detection circuit can provide the neural stimulation feedback signal based on the sensor(s) 730 and the contextual input(s) 731. The contextual input(s) can be used to avoid incomplete data from affecting the neural stimulation. Examples of contextual inputs include an activity sensor, a posture sensor and a timer. Any one or combination of two or more contextual inputs can be used by the feedback detection circuit. For example, an elevated heart rate may be representative of exercise rather than a reason for titrating the neural stimulation therapy. The therapy titration/adjustment module 732 uses the feedback signal (including data derived from monitored side effects and including data derived from a monitored therapy response) to modulate or titrate the therapy generated by the stimulation output circuit 707 to provide the desired therapy response while reducing or avoiding potential side effects attributable to the neural stimulation.

Figure 8:
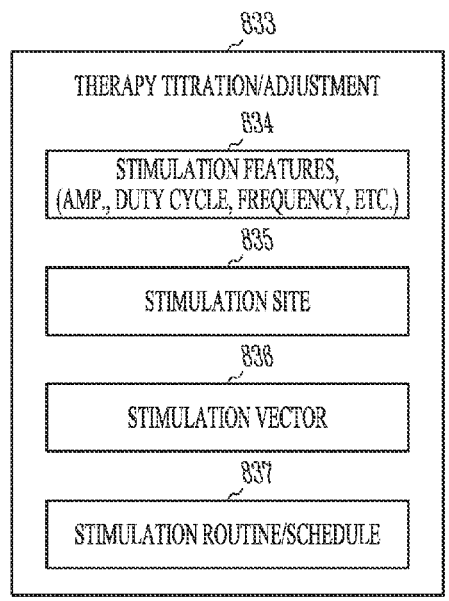
FIG. 8 illustrates an embodiment of a neural stimulation therapy titration/adjustment module.

FIG. 8 illustrates an embodiment of a neural stimulation therapy titration/adjustment module. The figure illustrates various means for titrating or modulating the intensity of the neural stimulation. According to various embodiments, titrating the therapy intensity 833 includes changing a stimulation feature 834 (e.g. amplitude, pulse duration, frequency, and/or waveform—including, for example, a phase-specific feature in a biphasic pulse), neural target site 835 (via multiple electrodes), and/or vector 836 (via the same or different vectors). Various embodiments titrate therapy by changing the electrodes used to provide the electrical therapy. Thus, given eN electrodes, the therapy can change from using a first set of electrodes selected from the eN electrodes to a second set of electrodes selected from the N electrodes. An electrode can be in one set but not the other, or can be in both sets. Some sets only include electrodes that are not in the other set. Various embodiments perform an iterative process where a stimulation is changed and the response is monitored. If appropriate after a designated time course or predetermined event (e.g. the therapy is not avoiding the side effect) the device will precede to the next stimulation routine 837.

Figure 9:
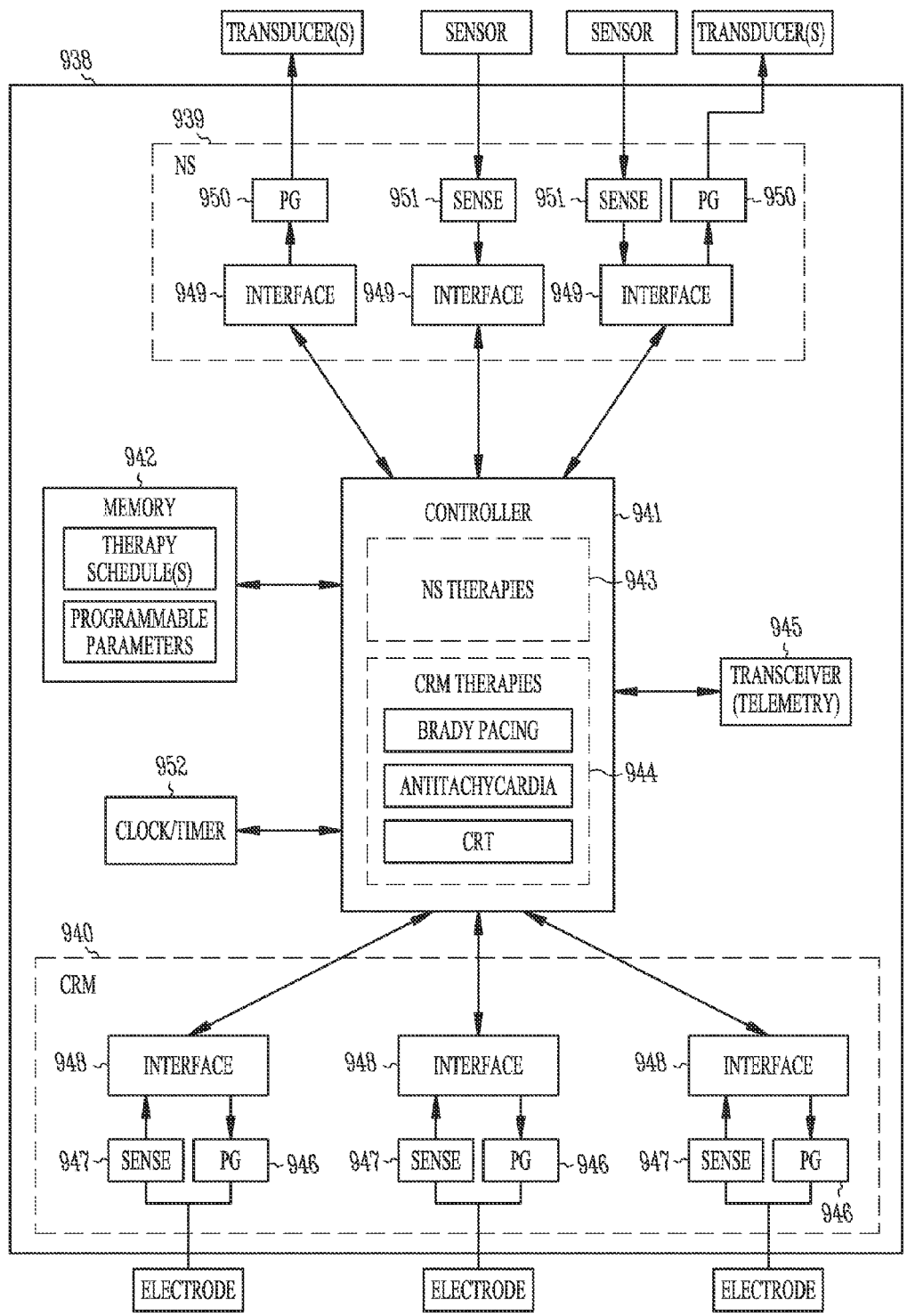
FIG. 9 illustrates an implantable medical device (IMD) having a neural stimulation (NS) component and a cardiac rhythm management (CRM) component, according to various embodiments of the present subject matter.

FIG. 9 illustrates an implantable medical device (IMD) 938 having a neural stimulation (NS) component 939 and a cardiac rhythm management (CRM) component 940 according to various embodiments of the present subject matter. The illustrated device includes a controller 941 and memory 942. According to various embodiments, the controller includes hardware, software, or a combination of hardware and software to perform the neural stimulation and CRM functions. For example, the programmed therapy applications discussed in this disclosure are capable of being stored as computer-readable instructions embodied in memory and executed by a processor. For example, therapy schedule(s) and programmable parameters can be stored in memory. According to various embodiments, the controller includes a processor to execute instructions embedded in memory to perform the neural stimulation and CRM functions. The illustrated neural stimulation therapy 943 can include any neural stimulation therapy, such as a therapy for ventricular remodeling. Various embodiments include CRM therapies 944, such as bradycardia pacing, anti-tachycardia therapies such as ATP, defibrillation and cardioversion, and cardiac resynchronization therapy (CRT). The illustrated device further includes a transceiver 945 and associated circuitry for use to communicate with a programmer or another external or internal device. Various embodiments include a telemetry coil.

The CRM therapy section 940 includes components, under the control of the controller, to stimulate a heart and/or sense cardiac signals using one or more electrodes. The illustrated CRM therapy section includes a pulse generator 946 for use to provide an electrical signal through an electrode to stimulate ahead, and further includes sense circuitry 947 to detect and process sensed cardiac signals. An interface 948 is generally illustrated for use to communicate between the controller 941 and the pulse generator 946 and sense circuitry 947. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 939 includes components, under the control of the controller, to stimulate a neural stimulation target and/or sense parameters associated with nerve activity or surrogates of nerve activity such as blood pressure and respiration. Three interfaces 949 are illustrated for use to provide neural stimulation. However, the present subject matter is not limited to a particular number interfaces, or to any particular stimulating or sensing functions. Pulse generators 950 are used to provide electrical pulses to transducer or transducers for use to stimulate a neural stimulation target. According to various embodiments, the pulse generator includes circuitry to set, and in some embodiments change, the amplitude of the stimulation pulse, the pulse width of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. Sense circuits 951 are used to detect and process signals from a sensor, such as a sensor of nerve activity, blood pressure, respiration, and the like. The interfaces 949 are generally illustrated for use to communicate between the controller 944 and the pulse generator 950 and sense circuitry 951. Each interface, for example, my be used to control a separate lead. Various embodiments of the NS therapy section only includes a pulse generator to stimulate a neural target. The illustrated device further includes a clock/timer 952, which can be used to deliver the programmed therapy according to a programmed stimulation protocol and/or schedule.

Figure 10:
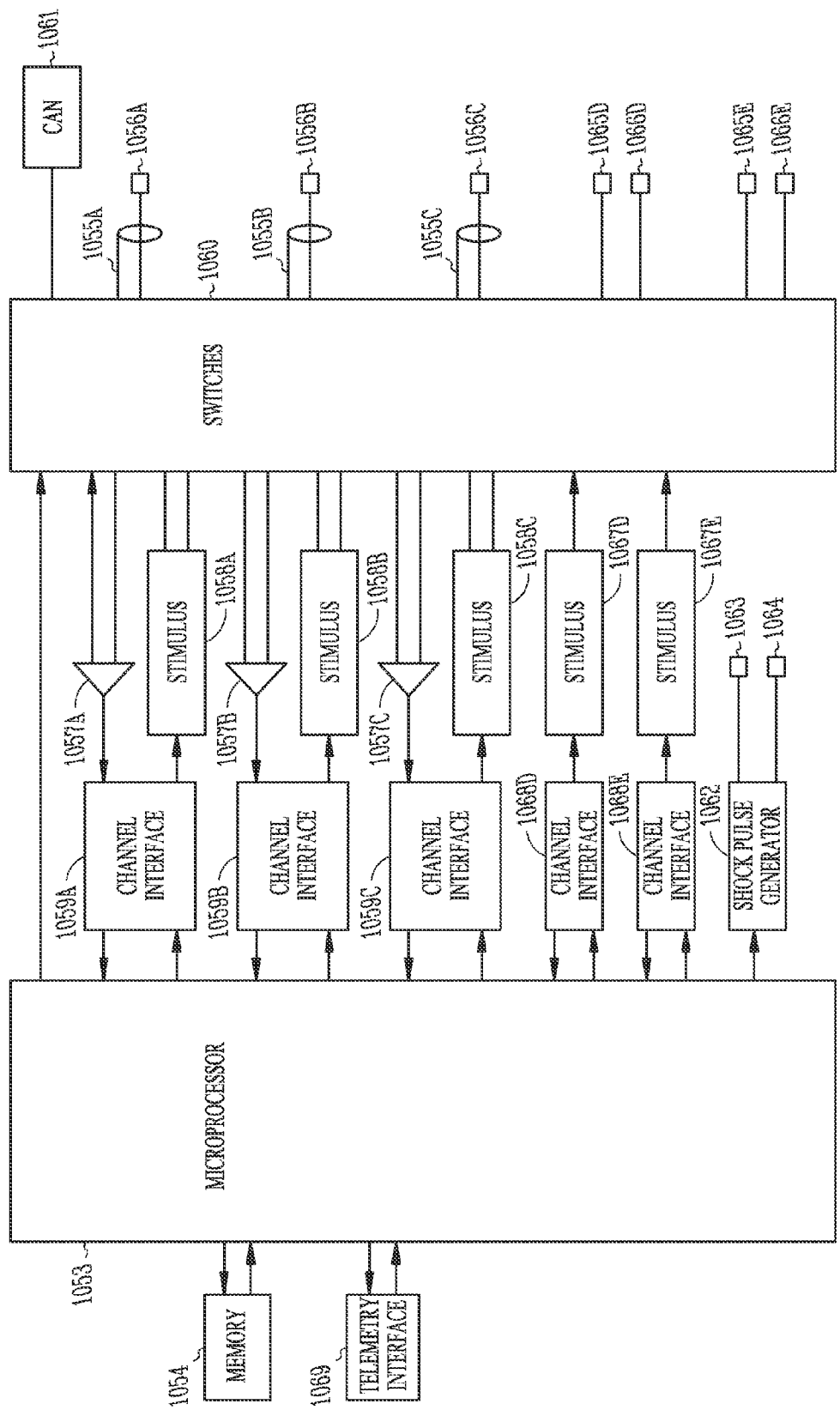
FIG. 10 shows a system diagram of an embodiment of a microprocessor-based implantable device, according to various embodiments.

FIG. 10 shows a system diagram of an embodiment of a microprocessor-based implantable device, according to various embodiments. The controller of the device is a microprocessor 1053 which communicates with a memory 1054 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 1055A-C and tip electrodes 1056A-C, sensing amplifiers 1057A-C, pulse generators 1058A-C, and channel interfaces 1059A-C. Each channel thus includes a pacing channel made up of the pulse generator connected to the electrode and a sensing channel made up of the sense amplifier connected to the electrode. The channel interfaces 1059A-C communicate bidirectionally with the microprocessor 1053, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a switching network 1060 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 1061 or an electrode on another lead serving as a ground electrode. A shock pulse generator 1062 is also interfaced to the controller for delivering a defibrillation shock via shock electrodes 1063 and 1064 to the atria or ventricles upon detection of a shockable tachyarrhythmia.

Neural stimulation channels, identified as channels D and E, are incorporated into the device for delivering parasympathetic stimulation and/or sympathetic inhibition, where one channel includes a bipolar lead with a first electrode 1065D and a second electrode 1066D, a pulse generator 1067D, and a channel interface 1068D, and the other channel includes a bipolar lead with a first electrode 1065E and a second electrode 1066E, a pulse generator 1067E, and a channel interface 1068E. Other embodiments may use unipolar leads in which case the neural stimulation pulses are referenced to the can or another electrode. In various embodiments, the pulse generator for each channel outputs a train of neural stimulation pulses which may be varied by the controller as to amplitude, frequency, duty-cycle, and the like. In this embodiment, each of the neural stimulation channels uses a lead which can be intravascularly disposed near an appropriate neural target. Other types of leads and/or electrodes may also be employed. A nerve cuff electrode may be used in place of an intravascularly disposed electrode to provide neural stimulation. In some embodiments, the leads of the neural stimulation electrodes are replaced by wireless links.

The figure illustrates a telemetry interface 1069 connected to the microprocessor, which can be used to communicate with an external device. The illustrated microprocessor 1053 is capable of performing neural stimulation therapy routines and myocardial (CRM) stimulation routines. Examples of NS therapy routines include a therapies to provide physical conditioning and therapies to treat ventricular remodeling, hypertension, sleep disordered breathing, blood pressure control such as to treat hypertension, cardiac rhythm management, myocardial infarction and ischemia, heart failure, epilepsy, depression, for pain, migraines, eating disorders and obesity, and movement disorders. The present subject matter is not limited to a particular neural stimulation therapy. Examples of myocardial therapy routines include bradycardia pacing therapies, anti-tachycardia shock therapies such as cardioversion or defibrillation therapies, anti-tachycardia pacing therapies (ATP), and cardiac resynchronization therapies (CRT).

System Embodiments

Figure 11:
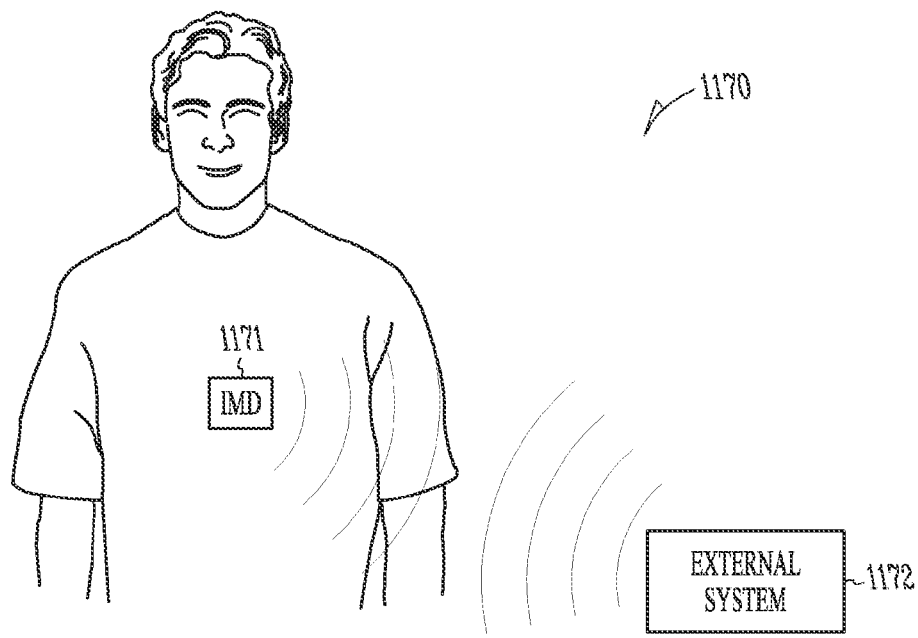
FIG. 11 illustrates a system including an implantable medical device (IMD) and an external system or device, according to various embodiments of the present subject matter.

FIG. 11 illustrates a system 1170 including an implantable medical device (IMD) 1171 and an external system or device 1172, according to various embodiments of the present subject matter. Various embodiments of the IMD include a combination of NS and CRM functions. The IMD may also deliver biological agents and pharmaceutical agents. The external system and the IMD are capable of wirelessly communicating data and instructions. In various embodiments, for example, the external system and IMD use telemetry coils to wirelessly communicate data and instructions. Thus, the programmer can be used to adjust the programmed therapy provided by the IMD, and the IMD can report device data (such as battery and lead resistance) and therapy data (such as sense and stimulation data) to the programmer using radio telemetry, for example. According to various embodiments, the IMD stimulates/inhibits a neural target to provide a neural stimulation therapy with the capability to avoid or diminish side effects from the neural stimulation. For example, an embodiment delivers vagus nerve stimulation and avoids or diminishes coughs attributable to the neural stimulation.

The external system allows a user such as a physician or other caregiver or a patient to control the operation of the IMD and obtain information acquired by the IMD. In one embodiment, external system includes a programmer communicating with the IMD bi-directionally via a telemetry link. In another embodiment, the external system is a patient management system including an external device communicating with a remote device through a telecommunication network. The external device is within the vicinity of the IMD and communicates with the IMD bi-directionally via a telemetry link. The remote device allows the user to monitor and treat a patient from a distant location. The patient monitoring system is further discussed below.

The telemetry link provides for data transmission from implantable medical device to external system. This includes, for example, transmitting real-time physiological data acquired by IMD, extracting physiological data acquired by and stored in IMD, extracting therapy history data stored in implantable medical device, and extracting data indicating an operational status of the IMD (e.g., battery status and lead impedance). Telemetry link also provides for data transmission from external system to IMD. This includes, for example, programming the IMD to acquire physiological data, programming IMD to perform at least one self-diagnostic test (such as for a device operational status), and programming the IMD to deliver at least one therapy.

Figure 12:
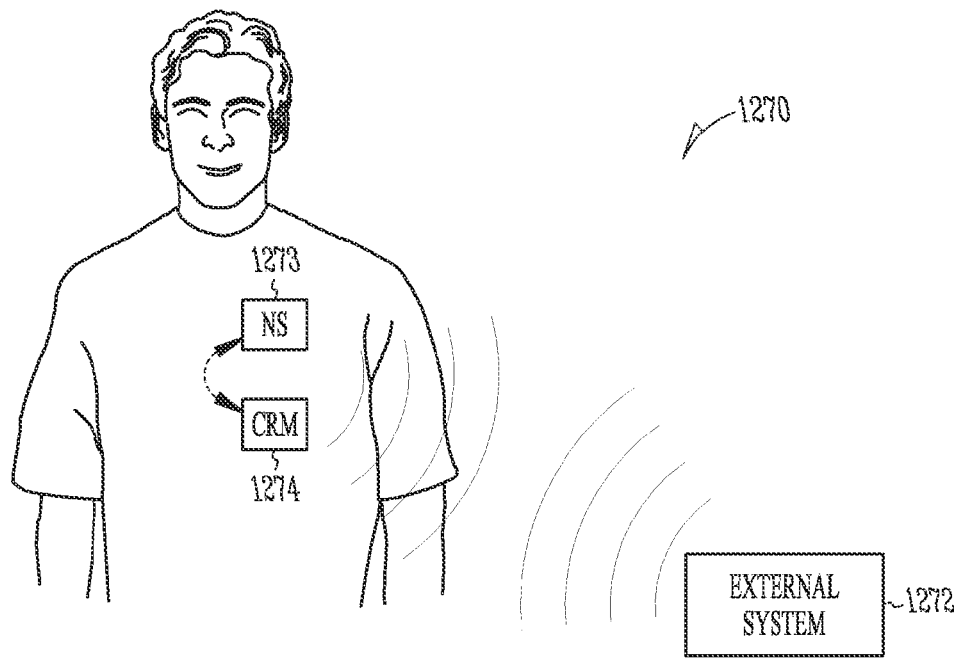
FIG. 12 illustrates a system including an external device, an implantable neural stimulator (NS) device and an implantable cardiac rhythm management (CRM) device, according to various embodiments of the present subject matter.

FIG. 12 illustrates a system 1270 including an external device 1272, an implantable neural stimulator (NS) device 1273 and an implantable cardiac rhythm management (CRM) device 1274, according to various embodiments of the present subject matter. Various aspects involve a method for communicating between an NS device and a CRM device or other cardiac stimulator. In various embodiments, this communication allows one of the devices 1273 or 1274 to deliver more appropriate therapy (i.e. more appropriate NS therapy or CRM therapy) based on data received from the other device. Some embodiments provide on-demand communications. In various embodiments, this communication allows each of the devices to deliver more appropriate therapy (i.e. more appropriate NS therapy and CRM therapy) based on data received from the other device. The illustrated NS device and the CRM device are capable of wirelessly communicating with each other, and the external system is capable of wirelessly communicating with at least one of the NS and the CRM devices. For example, various embodiments use telemetry coils to wirelessly communicate data and instructions to each other. In other embodiments, communication of data and/or energy is by ultrasonic means. Rather than providing wireless communication between the NS and CRM devices, various embodiments provide a communication cable or wire, such as an intravenously-fed lead, for use to communicate between the INS device and the CRM device. In some embodiments, the external system functions as a communication bridge between the NS and CRM devices.

FIGS. 13-16 illustrate system embodiments adapted to provide vagal stimulation, and are illustrated as bilateral systems that can stimulate both the left and right vagus nerve. Those of ordinary skill in the art will understand, upon reading and comprehending this disclosure, that systems can be designed to stimulate only the right vagus nerve, systems can be designed to stimulate only the left vagus nerve, and systems can be designed to bilaterally stimulate both the right and left vagus nerves.

Figure 13:
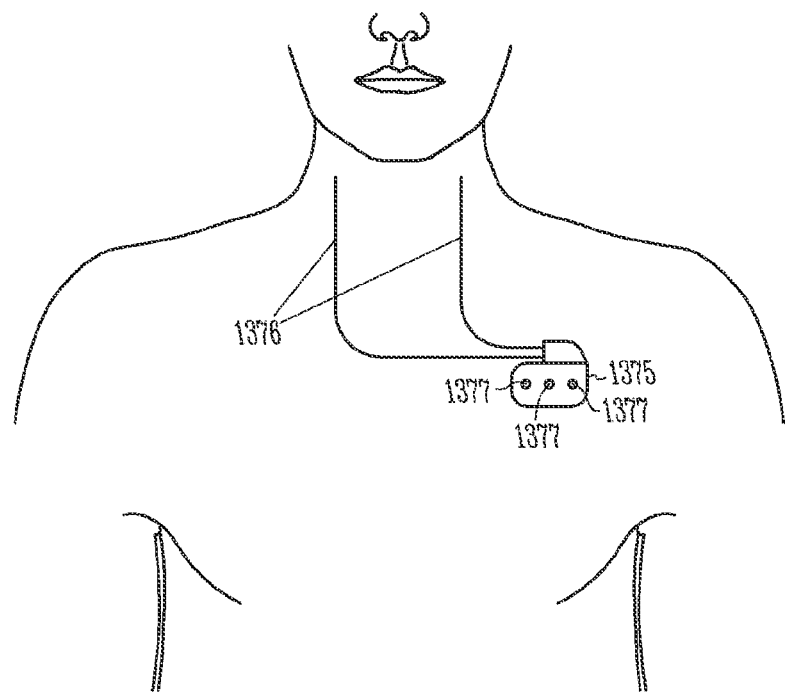
FIG. 13 illustrates a system embodiment in which an IMD is placed subcutaneously or submuscularly in a patient's chest with lead(s) positioned to stimulate a vagus nerve.

FIG. 13 illustrates a system embodiment in which an IMD 1375 is placed subcutaneously or submuscularly in a patient's chest with lead(s) 1376 positioned to stimulate a vagus nerve. According to various embodiments, neural stimulation lead(s) 1376 are subcutaneously tunneled to a neural target, and can have a nerve cuff electrode to stimulate the neural target. Some vagus nerve stimulation lead embodiments are intravascularly fed into a vessel proximate to the neural target, and use electrode(s) within the vessel to transvascularly stimulate the neural target. For example, some embodiments stimulate the vagus using electrode(s) positioned within the internal jugular vein. Other embodiments deliver neural stimulation to the neural target from within the trachea, the laryngeal branches of the internal jugular vein, and the subclavian vein. The neural targets can be stimulated using other energy waveforms, such as ultrasound and light energy waveforms. Other neural targets can be stimulated, such as cardiac nerves and cardiac fat pads. The illustrated system includes leadless ECG electrodes on the housing of the device. These ECG electrodes 1377 are capable of being used to detect heart rate, for example.

Figure 14:
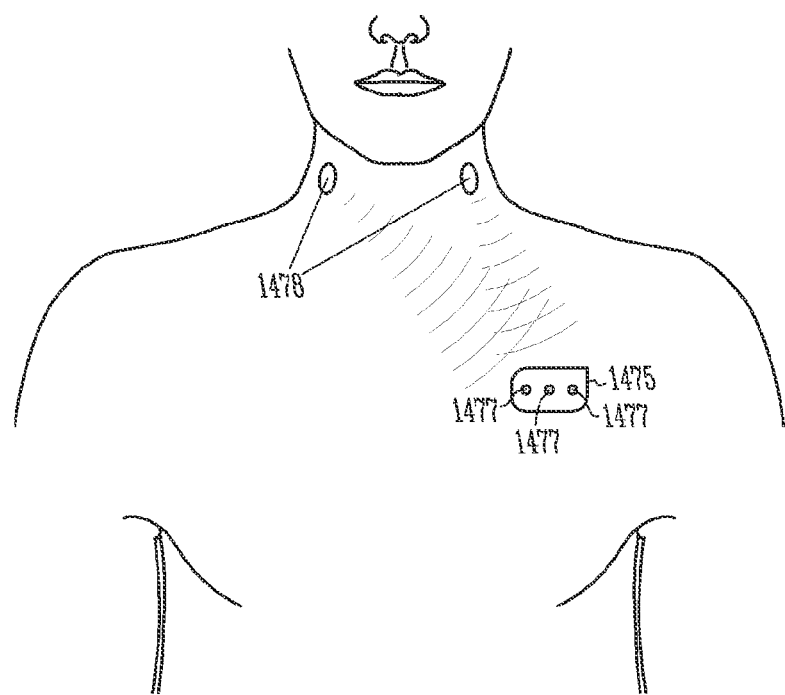
FIG. 14 illustrates a system embodiment that includes an implantable medical device (IMD) with satellite electrode(s) positioned to stimulate at least one neural target.

FIG. 14 illustrates a system embodiment that includes an implantable medical device (IMD) 1475 with satellite electrode(s) 1478 positioned to stimulate at least one neural target. The satellite electrode(s) are connected to the IMD, which functions as the planet for the satellites, via a wireless link. Stimulation and communication can be performed through the wireless link. Examples of wireless links include RF links and ultrasound links. Examples of satellite electrodes include subcutaneous electrodes, nerve cuff electrodes and intravascular electrodes. Various embodiments include satellite neural stimulation transducers used to generate neural stimulation waveforms such as ultrasound and light waveforms. The illustrated system includes leadless ECG electrodes on the housing of the device. These ECG electrodes 11477 are capable of being used to detect heart rate, for example.

Figure 15:
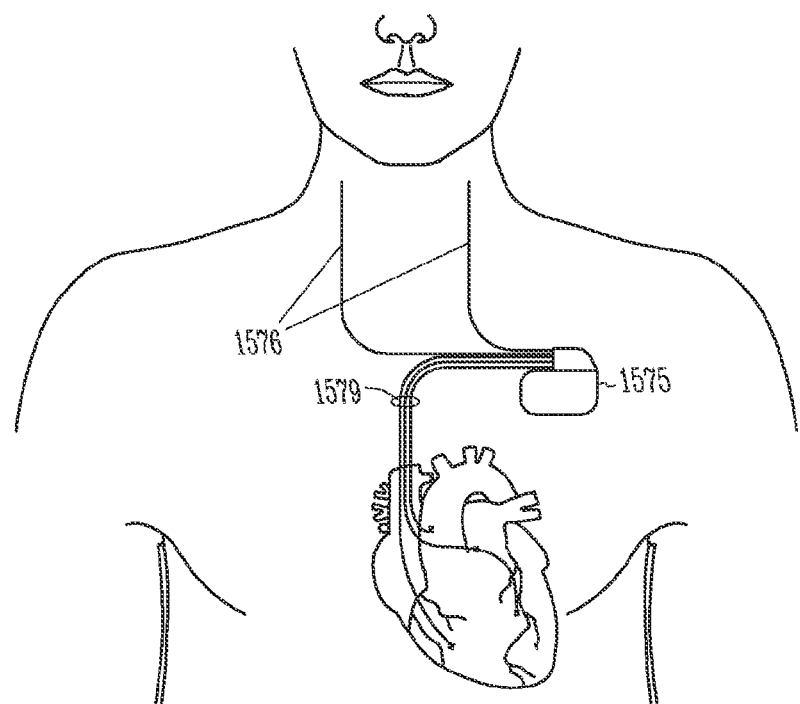
FIG. 15 illustrates an IMD placed subcutaneously or submuscularly in a patients chest with lead(s) positioned to provide a CRM therapy to a heart, and with lead(s) positioned to stimulate and/or inhibit neural traffic at a neural target, such as a vagus nerve, according to various embodiments.

FIG. 15 illustrates an IMD 1575 placed subcutaneously or submuscularly in a patient's chest with lead(s) 1579 positioned to provide a CRM therapy to a heart, and with lead(s) 1576 positioned to stimulate and/or inhibit neural traffic at a neural target, such as a vagus nerve, according to various embodiments. According to various embodiments, neural stimulation lead(s) are subcutaneously tunneled to a neural target, and can have a nerve cuff electrode to stimulate the neural target. Some lead embodiments are intravascularly fed into a vessel proximate to the neural target, and use transducer(s) within the vessel to transvascularly stimulate the neural target. For example, some embodiments target the vagus nerve using electrode(s) positioned within the internal jugular vein.

Figure 16:
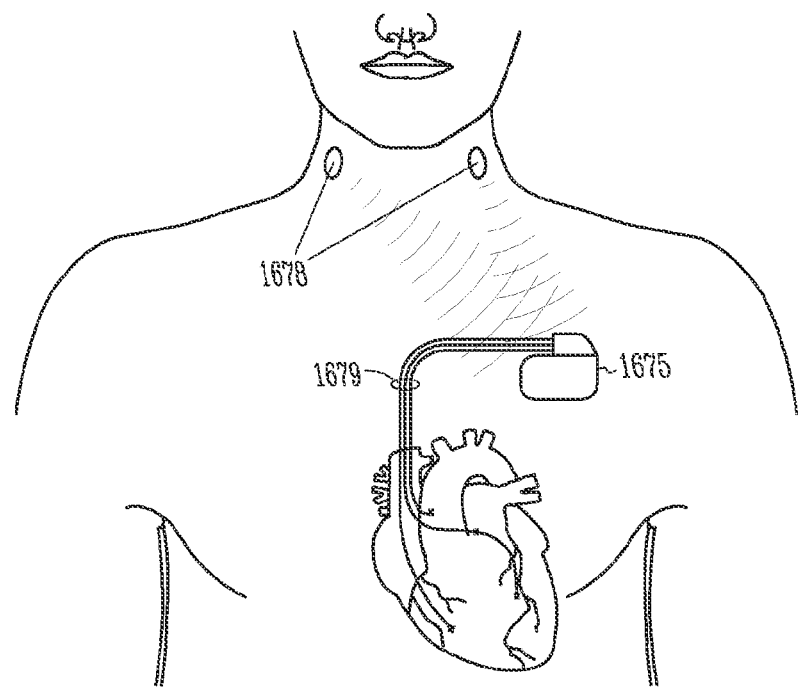
FIG. 16 illustrates an MID with lead(s) positioned to provide a CRM therapy to a heart, and with satellite transducers positioned to stimulate/inhibit a neural target such as a vagus nerve, according to various embodiments.

FIG. 16 illustrates an IMD 1675 with lead(s) 1679 positioned to provide a CRM therapy to a heart, and with satellite transducers 1678 positioned to stimulate/inhibit a neural target such as a vagus nerve, according to various embodiments. The satellite transducers are connected to the IMD, which functions as the planet for the satellites, via a wireless link. Stimulation and communication can be performed through the wireless link. Examples of wireless links include RF links and ultrasound links. Although not illustrated, some embodiments perform myocardial stimulation using wireless links. Examples of satellite transducers include subcutaneous electrodes, nerve cuff electrodes and intravascular electrodes.

Figure 17:
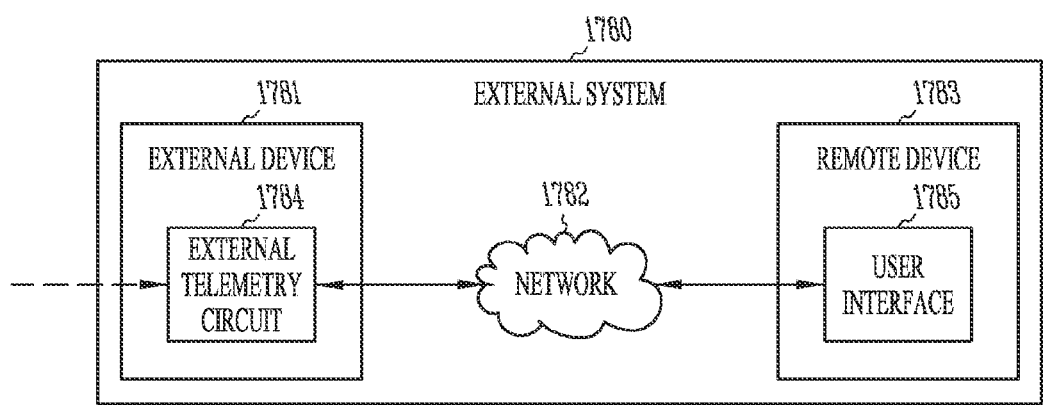
FIG. 17 is a block diagram illustrating an embodiment of an external system.

FIG. 17 is a block diagram illustrating an embodiment of an external system 1780. The external system includes a programmer, in some embodiments. In the illustrated embodiment, the external system includes a patient management system. As illustrated, the external system 1780 is a patient management system including an external device 1781, a telecommunication network 1782, and a remote device 1783. The external device 1781 is placed within the vicinity of an implantable medical device (IMD) and includes an external telemetry system 1784 to communicate with the IMD. The remote device(s) 1783 is in one or more remote locations and communicates with the external device 1781 through the network 1782, thus allowing a physician or other caregiver to monitor and treat a patient from a distant location and/or allowing access to various treatment resources from the one or more remote locations. The illustrated remote device 1783 includes a user interface 1785. According to various embodiments, the external device 1781 includes a neural stimulator, a programmer or other device such as a computer, a personal data assistant or phone. The external device 1781, in various embodiments, includes two devices adapted to communicate with each other over an appropriate communication channel, such as a computer by way of example and not limitation. The external device can be used by the patient or physician to provide side effect feedback indicative of patient discomfort, for example.

One of ordinary skill in the art will understand that the modules and other circuitry shown and described herein can be implemented using software, hardware, and combinations of software and hardware. As such, the term module is intended to encompass software implementations, hardware implementations, and software and hardware implementations.

The methods illustrated in this disclosure are not intended to be exclusive of other methods within the scope of the present subject matter. Those of ordinary skill in the an will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A system, comprising:
 a neural stimulation delivery system configured to deliver a neural stimulation signal;
 a sensor configured to sense a parameter to provide a signal for use in detecting a side effect;
 a side effect detector configured to receive the signal from the sensor, to characterize the signal as a detected side effect, and to provide a detected side effect signal;
 a controller configured to control the neural stimulation delivery system to provide a neural stimulation therapy, receive the detected side effect signal from the side effect detector determine whether the neural stimulation therapy caused the detected side effect, and automatically adjust the neural stimulation therapy if it is determined that the delivered neural stimulation therapy caused the detected side effect, wherein the side effect is selected from the group of side effects consisting of: a voice-related side effect, a respiratory-related side effect and a cardiac output side effect.

2. The system of claim 1, wherein the detected side effect is voice alteration.

3. The system of claim 1, wherein the detected side effect is voice laryngismus.

4. The system of claim 1, wherein the detected side effect is dyspnea.

5. The system of claim 1, wherein the detected side effect is apnea.

6. The system of claim 1, wherein the controller is configured to automatically adjust the neural stimulation therapy to prevent or diminish future occurrences of the detected side effect.

7. The system of claim 1, wherein the neural stimulation signal includes a biphasic waveform, and the controller is adapted to independently adjust at least one stimulation parameter for at least one phase in the biphasic waveform.

8. The system of claim 7, further comprising a charge balance monitor adapted to monitor a charge balance at least two neural stimulation electrodes and to adjust the at least one stimulation parameter for the at least one phase in the biphasic waveform to maintain a charge balance to acceptable levels.

9. The system of claim 7, wherein the at least one stimulation parameter includes an amplitude or a pulse width.

10. The system of claim 7, wherein the neural stimulation signal includes a biphasic waveform with a first phase and a second phase, and the controller is adapted to independently adjust at least one stimulation parameter for the second phase in the waveform to prevent or diminish future side effects attributable to the neural stimulation therapy and maintain the stimulation parameters for the first phase to continue to deliver the neural stimulation therapy.

11. The system of claim 1, wherein the neural stimulation therapy includes a heart failure therapy or a hypertension therapy.

12. The system of claim 1, wherein the neural stimulation therapy includes intermittent neural stimulation with a schedule of stimulation ON and stimulation OFF times, and the controller is configured to determine if the detected side effect occurred during one of the stimulation ON times.

13. A system, comprising:
a neural stimulation delivery system configured to deliver a neural stimulation signal;
a sensor configured to sense a parameter to provide a signal for use in detecting a voice-related side effect;
a side effect detector configured to receive the signal from the sensor, to characterize the signal as a detected voice-related side effect, and to provide a detected side effect signal; and
a controller configured to control the neural stimulation delivery system to provide a neural stimulation therapy, receive the detected side effect signal from the side effect detector, determine whether delivered neural stimulation therapy caused the detected voice-related side effect, and automatically adjust the neural stimulation therapy if it is determined that the delivered neural stimulation therapy caused the detected voice-related side effect.

14. The system of claim 13, wherein the neural stimulation therapy includes a vagal stimulation therapy.

15. A system, comprising:
a neural stimulation delivery system configured to deliver a neural stimulation signal;
a sensor configured to sense a parameter to provide a signal for use in detecting a respiratory-related side effect;
a side effect detector configured to receive the signal from the sensor, to characterize the signal as a detected respiratory-related side effect, and to provide a detected side effect signal; and
a controller configured to control the neural stimulation delivery system to provide a neural stimulation therapy, receive the detected side effect signal from the side effect detector, determine whether delivered neural stimulation therapy caused the detected respiratory-related side effect, and automatically adjust the neural stimulation therapy if it is determined that the delivered neural stimulation therapy caused the detected respiratory-related side effect.

16. The system of claim 15, wherein the neural stimulation therapy includes a vagal stimulation therapy.

17. A system, comprising:
a neural stimulation delivery system configured to deliver a neural stimulation signal;
a sensor configured to sense a parameter to provide a signal for use in detecting cardiac output;
a side effect detector configured to receive the signal from the sensor, to characterize the signal as a detected cardiac output side effect, and to provide a detected side effect signal; and
a controller configured to control the neural stimulation delivery system to provide a neural stimulation therapy, receive the detected side effect signal from the side effect detector, determine whether delivered neural stimulation therapy caused the detected cardiac output side effect, and automatically adjust the neural stimulation therapy if it is determined that the delivered neural stimulation therapy caused the detected cardiac output side effect.

18. The system of claim 17, wherein the sensor includes a flow sensor.

19. A method for operating an implantable medical device, comprising:
using the implantable medical device to deliver a neural stimulation therapy;
using the implantable medical device to determine whether the neural stimulation therapy causes a side effect from the group of side effects consisting of: a voice-related side effect, a respiratory-related side effect and a cardiac output side effect; and
automatically adjusting the neural stimulation therapy if it is determined that the neural stimulation therapy causes the side effect.

20. The method of claim 19, wherein using the implantable medical device to deliver a neural stimulation therapy includes using the implantable medical device to deliver vagal stimulation therapy.

* * * * *